United States Patent [19]
Kim et al.

[11] Patent Number: 5,498,615
[45] Date of Patent: Mar. 12, 1996

[54] QUINOLONE CARBOXYLIC ACID DERIVATIVES AND PROCESS FOR PREPARING THE SAME

[75] Inventors: Wan J. Kim; Tae H. Park; Moon H, Kim; Tae S. Lee; Keun S. Nam, all of Daejeon, Rep. of Korea

[73] Assignee: Korea Research Institute of Chemical Technology, Daejeon, Rep. of Korea

[21] Appl. No.: 277,602

[22] Filed: Jul. 20, 1994

Related U.S. Application Data

[63] Continuation-in-part of Ser. No. 52,711, Apr. 26, 1993, abandoned.

[51] Int. Cl.$^6$ .................... A61K 31/405; C07D 471/02
[52] U.S. Cl. .................... 514/300; 546/123; 546/156
[58] Field of Search .................... 546/123, 156; 514/300

[56] References Cited

U.S. PATENT DOCUMENTS

| | | | |
|---|---|---|---|
| 4,146,719 | 3/1979 | Irikura . | |
| 4,563,459 | 1/1986 | Grohe et al. . | |
| 4,954,507 | 9/1990 | Weber et al. . | |
| 4,965,273 | 10/1990 | Weber et al. . | |
| 4,990,517 | 2/1991 | Petersen et al. . | |
| 5,017,581 | 5/1991 | Nishitani et al. . | |
| 5,059,597 | 10/1991 | Petersen et al. . | |
| 5,091,384 | 2/1992 | Kim et al. . | |
| 5,140,033 | 8/1992 | Schriewer et al. . | |
| 5,202,337 | 4/1993 | Petersen et al. . | |
| 5,221,676 | 6/1993 | Laborde et al. | 546/123 |
| 5,229,396 | 7/1993 | Brighty | 546/123 |
| 5,245,037 | 9/1993 | Kuramoto et al. | 546/123 |
| 5,262,417 | 11/1993 | Gammill et al. | 546/123 |
| 5,281,596 | 1/1994 | Kitao et al. | 546/123 |
| 5,281,612 | 1/1994 | Domagala et al. | 546/123 |
| 5,284,842 | 2/1994 | Petersen et al. | 546/123 |

FOREIGN PATENT DOCUMENTS

| | | |
|---|---|---|
| 0009425 | 2/1980 | European Pat. Off. . |
| 0047005 | 10/1982 | European Pat. Off. . |
| 0304087 | 2/1989 | European Pat. Off. . |
| 0326916 | 8/1989 | European Pat. Off. . |
| 0366643 | 5/1990 | European Pat. Off. . |
| 0424850 | 5/1991 | European Pat. Off. . |
| 0424851 | 5/1991 | European Pat. Off. . |
| 0520277 | 6/1992 | European Pat. Off. . |
| 0516861 | 9/1992 | European Pat. Off. . |
| 0549857 | 9/1992 | European Pat. Off. . |
| 0588166 | 3/1994 | European Pat. Off. . |
| 3514076 | 10/1985 | Germany . |
| 3632222 | 4/1988 | Germany . |
| 9006307 | 6/1990 | WIPO . |
| 9116310 | 10/1991 | WIPO . |
| 9402479 | 2/1994 | WIPO . |

OTHER PUBLICATIONS

D. Bouzard et al., "Fluoronaphtyridines as Antibacterial Agents. 4. Synthesis and Structure–Activity Relationships of 5-Substituted-6-fluoro-7-(cycloalkylamino)-1,4-dihydro-4-oxo-1,8-naphthyridine-3-carboxylic Acids", *J. Med. Chem.*, vol. 35, No. 3, pp. 518–525 (1992).

Daniel T. W. Chu et al., "Synthesis and Structure–Activity Relationships of New Arylfluoronaphthyridine Antibacterial Agents", *J. Med. Chem.*, vol. 29, No. 11, pp. 2363–2369 (1986).

John M. Domagala et al., "7–Substituted 5-Amino-1-cyclopropyl-6,8-difluoro-1,4-dihydro-4-oxo-3-quinolinecarboxylic Acids: Synthesis and Biological Activity of a New Class of Quinolone Antibacterials", *J. Med. Chem.*, vol. 31, No. 3, pp. 503–506 (1988).

H. Saito et al., "AM–1091", *Drugs of the Future*, vol. 14, No. 10, pp. 931–935 (1989).

*Primary Examiner*—Johann Richter
*Assistant Examiner*—John Peabody
*Attorney, Agent, or Firm*—Brumbaugh, Graves, Donohue & Raymond

[57] ABSTRACT

The present invention relates to novel quinolone carboxylic acid derivatives having useful antibacterial activities of formula (I):

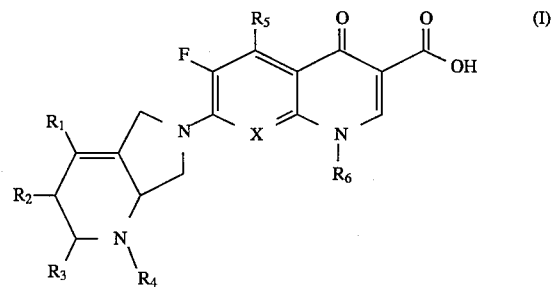

wherein, $R_1$, $R_2$, and $R_3$, which may be the same or different, are each hydrogen or a halogen atom, or a lower alkyl group optionally substituted with an amino or a hydroxy group;

$R_4$ is hydrogen atom, a lower alkyl, benzyl, t-butoxycarbonyl or ethoxycarbonyl group;

$R_5$ is hydrogen, chlorine atom, methyl or an amino group;

$R_6$ is a lower alkyl group, or a cyclopropyl or a phenyl group optionally substituted with a halogen atom; and X is a methyne group optionally substituted with a lower alkyl or a lower alkoxy group or a halogen atom, and pharmaceutically acceptable salts thereof, and processes for preparing these compounds. The present invention also relates to novel intermediates which are useful for preparing the quinolone compounds of the invention.

6 Claims, No Drawings

QUINOLONE CARBOXYLIC ACID DERIVATIVES AND PROCESS FOR PREPARING THE SAME

CROSS REFERENCE

This application is a continuation-in-part of U.S. patent application Ser. No. 08/052,711, filed Apr. 26, 1993, now abandoned, which is incorporated by reference herein.

FIELD OF THE INVENTION

The present invention relates to novel quinolone carboxylic acid derivatives and pharmaceutically acceptable salts thereof which possess a broad spectrum of potent antibacterial activities and are useful as antibacterials and to processes for preparing these compounds.

DESCRIPTION OF THE PRIOR ART

Quinolone carboxylic acid-type antibacterials are known to exhibit strong antibacterial activity against aerobic Gram-negative bacteria. Among these quinolone carboxylic acid-type antibacterials, especially enoxacin, norfloxacin, ofloxacin, ciprofloxacin and tosufloxacin are clinically used. However, these prior art quinolones are known to have relatively weak activity against Gram-positive bacteria, while they have superior antibacterial activity against Gram-negative bacteria.

Therefore, the development of new quinolone carboxylic acid-type compounds which possess a broad spectrum of antibacterial activities and are effective against quinolone-resistant bacteria as well as methicillin-resistant *Staphylococcus aureus* (MRSA) is still needed.

SUMMARY OF THE INVENTION

In order to solve the above problems, the present inventors have conducted extensive studies to develop novel quionlone compounds.

As a result, it has been surprisingly found that quinolone carboxylic acid derivatives having the substituent represented by the following formula (A) at 7-position of quinolone nucleus meet the above requirements.

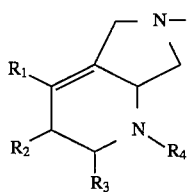
(A)

In the above formula, $R_1$, $R_2$ and $R_3$, which may be the same or different, are each hydrogen or a halogen atom, or a lower alkyl group optionally substituted with an amino or hydroxy group; and $R_4$ is hydrogen atom, a lower alkyl, benzyl, t-butoxycarbonyl or ethoxycarbonyl group.

Accordingly, the present invention is concerned with novel quinolone carboxylic acid derivatives and pharmaceutically acceptable salts thereof which can meet said requirements and with processes for preparing such compounds.

DETAILED DESCRIPTION OF THE INVENTION

An object of the present invention is to provide novel quinolone carboxylic acid derivatives and pharmaceutically acceptable salts thereof which possess a broad spectrum of antibacterial activities against various microorganisms, and to provide processes for preparing these compounds.

Another object of the present invention is to provide intermediates which are useful for producing the desired compounds of the present invention.

The present invention provides novel quinolone carboxylic acid derivatives represented by the formula (I):

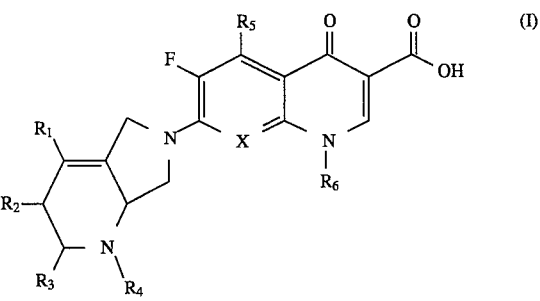

wherein, $R_1$, $R_2$, $R_3$ and $R_4$ are the same as defined above;

$R_5$ is hydrogen or chlorine atom, or methyl or an amino group;

$R_6$ is a lower alkyl group, or a cyclopropyl or a phenyl group optionally substituted with a halogen atom; and X is nitrogen atom, or a methyne group optionally substituted with a lower alkyl or a lower alkoxy group or a halogen atom, and their pharmaceutically acceptable salts.

The term "lower alkyl" used herein refers to a straight or branched $C_{1-4}$ alkyl such as methyl, ethyl, n-propyl, isopropyl, n-butyl, sec-butyl or tert-butyl.

The term "halogen atom" used herein refers to a chlorine, bromine, fluorine or iodine atom.

The term "lower alkoxy" used herein refers to $C_{1-4}$ alkoxy such as methoxy, ethoxy, n-propyloxy, iso-propyloxy, n-butyloxy, sec-butyloxy or tert-butyloxy.

Among the compounds of the present invention, the preferred compounds which possess a broad spectrum of antibacterial activities are as follows:

1-cyclopropyl-6,8-difluoro-7-[(2,8-diazabicyclo[4.3.0]non-5-en)-8-yl]- 1,4-dihydroquinoline-4-oxo-3-carboxylic acid;

1-cyclopropyl-6-fluoro-8-chloro-7-[(2,8-diazabicyclo [4.3.0]non-5-en)-8-yl]- 1,4-dihydroquinoline-4-oxo-3-carboxylic acid;

1-(2-fluorocyclopropyl)-6-fluoro-8-chloro-7-[(2,8-diazabicyclo[4.3.0]non-5-en)- 8-yl]-1,4-dihydroquinoline-4-oxo-3-carboxylic acid;

1-cyclopropyl-5,8-dichloro-6-fluoro-7-[(2,8-diazabicyclo [4.3.0]non-5-en)-8-yl]- 1,4-dihydroquinoline-4-oxo-3-carboxylic acid;

1-cyclopropyl-5-amino-6,8-difluoro-7-[(2,8-diazabicyclo [4.3.0]non-5-en)-8-yl]- 1,4-dihydroquinoline-4-oxo-3-carboxylic acid;

1-cyclopropyl-6,8-dichloro-7-[(2-methyl-2,8-diazabicyclo [4.3.0]non-5-en)-8-yl]- 1,4-dihydroquinoline-4-oxo-3-carboxylic acid;

1-(2-fluorocyclopropyl)-5,8-dichloro-6-fluoro-7-[(2,8-diazabicyclo[4.3.0]non- 5-en)-8-yl]-1,4-dihydroquinoline-4-oxo-3-carboxylic acid; and 1-cyclopropyl-6-fluoro-8-methoxy-7-[(2,8-diazabicyclo [4.3.0]non-5-en)-8-yl]- 1,4-dihydroquinoline-4-oxo-3-carboxylic acid.

Among the compounds of the present invention, the more preferred compounds which possess a broad spectrum of antibacterial activities are as follows:

1-cyclopropyl-6,8-difluoro-7-[(2,8-diazabicyclo[4.3.0]non-5-en)8-yl]- 1,4-dihydroquinoline-4-oxo-3-carboxylic acid;

1-cyclopropyl-6-fluoro-8-chloro-7-[(2,8-diazabicyclo [4.3.0]non-5-en)-8-yl]- 1,4-dihydroquinoline-4-oxo-3-carboxylic acid;

1-cyclopropyl-5,8-dichloro-6-fluoro-7-[(2,8-diazabicyclo [4.3.0]non-5-en)-8-yl]- 1,4-dihydroquinoline-4-oxo-3-carboxylic acid;

1-cyclopropyl-5-amino-6,8-difluoro-7-[(2,8-diazabicyclo [4.3.0]non-5-en)-8-yl]- 1,4-dihydroquinoline-4-oxo-3-carboxylic acid;

1-(2-fluorocyclopropyl)-6-fluoro-8-chloro-7-[(2,8-diazabicyclo[4.3.0] non-5-en)- 8-yl]-1,4-dihydroquinoline-4-oxo-3-carboxylic acid; and 1-cyclopropyl-6-fluoro-8-methoxy-7-[(2,8-diazabicyclo [4.3.0]non-5-en)-8-yl]- 1,4-dihydroquinoline-4-oxo-3-carboxylic acid.

The most preferred compounds which possess a broad spectrum of antibacterial activities are optical isomers of the compounds disclosed herein. Such optical isomers are described in more detail in the copending Wan Joo KIM, Tae Ho PARK, Jewn Giew PARK, Moon Hwan KIM, Bong Jin KIM, and Neil PEARSON, U.S. patent application Ser. No. 08/277,601 filed on Jul. 20, 1994 for "Novel Quinolone Derivatives and Processes for the Preparation Thereof" which is incorporated by reference herein.

Quinolone compounds represented by formula (I) according to the present invention can be prepared by either process (A) or (B) set forth hereinafter.

Process (A)

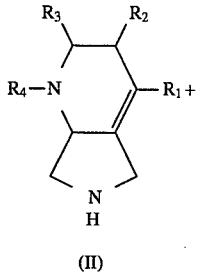

(II)

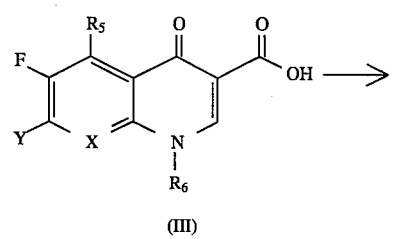

(III)

Process (A)
-continued

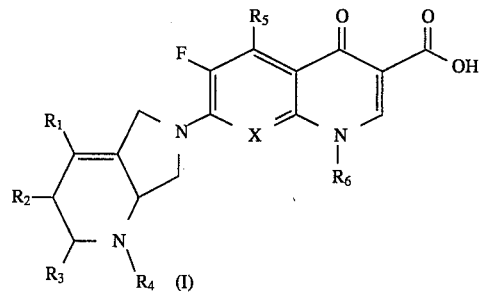

In the above formula, $R_1$, $R_2$, $R_3$, $R_4$, $R_5$, $R_6$ and X are the same as defined previously; and Y is a halogen atom or a mesyl or a tosyl group.

In accordance with the above process (A), quinolone compounds represented by formula (I) of the present invention can be prepared by reacting a compound of formula (II) with a compound of formula (III) in a solvent, preferably in the presence of an inorganic or organic base. Solvents used in this process include water, a lower alkanol, acetonitrile, pyridine, dimethylformamide, dimethylsulfoxide and a mixture thereof. Inorganic bases used herein include calcium carbonate, potassium carbonate and the like. Organic bases used herein include 1,8-diazabicyclo[5.4.0]undec-7-ene (DBU), triethylamine and the like. The above reaction may be carried out at a temperature between about 20° and about 200° C., preferably between about 60° and about 130° C. The reaction time is about 1 to about 24 hours.

Process (B)

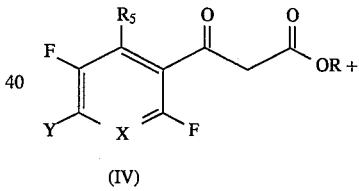

(IV)

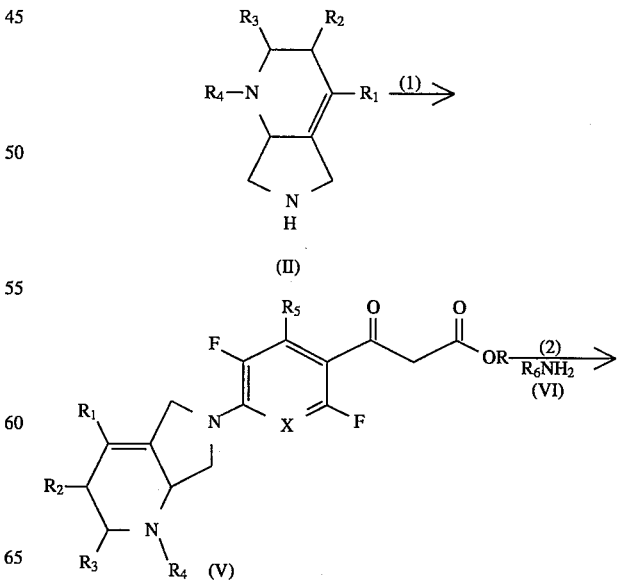

-continued
Process (B)

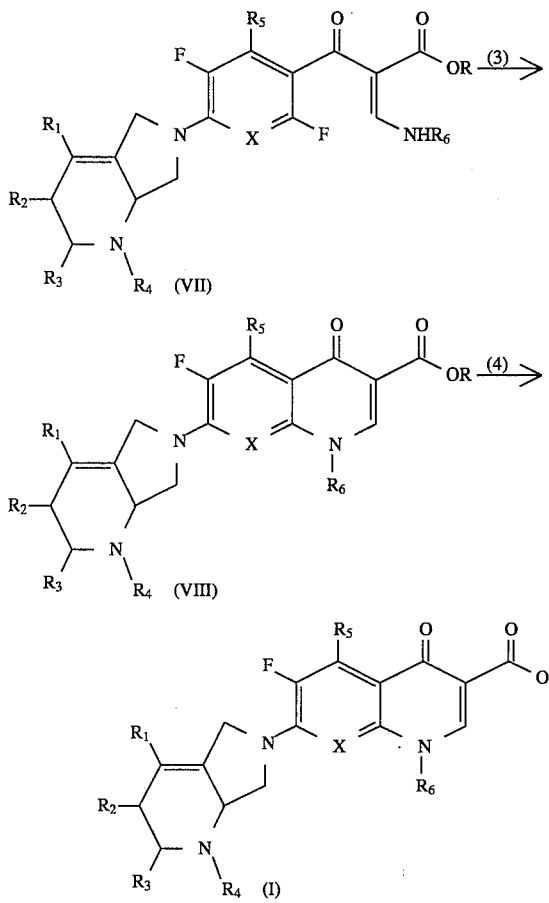

In the above formula, $R_1, R_2, R_3, R_4, R_5, R_6$, X and Y are the same as defined above; and R is hydrogen atom or a lower alkyl group.

The above Process (B) comprises the following four steps;

Step (1)

The compound of formula (V) can be prepared by reacting a compound of formula (IV) with a compound of formula (II). The above reaction can be conducted in the presence of a solvent such as a lower alkanol, acetonitrile, dimethylformamide, dimethylsulfoxide, tetrahydrofuran or a mixture thereof, preferably in the presence of an inorganic base such as sodium hydroxide and sodium carbonate or an organic base such as 1,8-diazabicyclo[5.4.0]undec-7-ene and triethylamine at a temperature ranging from about 0° C. to the refulx temperature of the solvent employed.

Step (2)

The compound formula (VII) can be obtained by condensing with an amine compound of formula (VI) after a compound of formula (V) is heated under reflux with ethyl orthoformate and acetic anhydride. The condensation reaction is preferably carried out with a solvent such as ethanol, dimethylsulfoxide, acetone, 1,4-dioxane or a mixture thereof at a temperature ranging from 0° to 50° C.

Step (3)

The compound of formula (VIII) can be obtained by cyclizing a compound of formula (VII); and said cyclization reaction is preferably carried out by employing a reaction solvent such as acetonitrile, dimethylformamide, dimethylsulfoxide, tetrahydrofuran or a mixture thereof, preferably in the presence of an inorganic base such as sodium hydride, potassium hydride, sodium fluoride and potassium fluoride or an organic base such as triethylamine and pyridine at a temperature ranging from 0° C. to the reflux temperature of the solvent employed.

Step (4)

The compound of formula (I) can be prepared by hydrolyzing a compound of formula (VIII) obtained from Step (3) above. The hydrolysis can be carried out by employing a conventional method such as acid or base treatment.

The intermediates obtained in process (B), i.e., the respective compounds of formula (V), (VII) and (VIII) are novel compounds; and therefore, the present invention also includes these compounds.

The compounds employed as starting materials in accordance with the present invention are commercially available and also can be obtained through known processes in the art.

For example, one of the compounds of formula (III) can be prepared by the following process (I) described in *J. Med. Chem.* 31, 503 (1988).

Process (I)

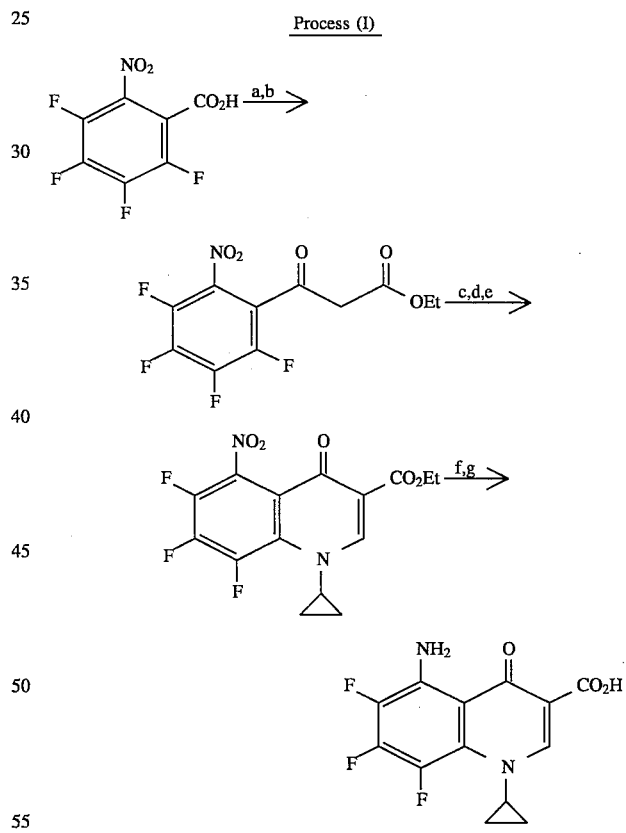

a: $(COCl)_2$, $H_2CCl_2$, DMF; b: malonic monoester dianion; c: $HC(OEt)_3$, $Ac_2O$; d: $c-C_3H_5-NH_2$; e: t-BuOK, t-BuOH; f: RaNi; g: HCl.

The 6-nitro-2,3,4,5-tetrafluorobenzoic acid was converted to the keto ester with dianion of malonic half ester (step 1) and finally to 5-amino-1-cyclopropyl-6,7,8-trifluoro-1,4-dihydro-4-oxo-3-quinoline carboxylic acid by the general route reported by Chu, D. T. *J. Heterocycl. Chem.* 22, 1033 (1985).

Process (II)
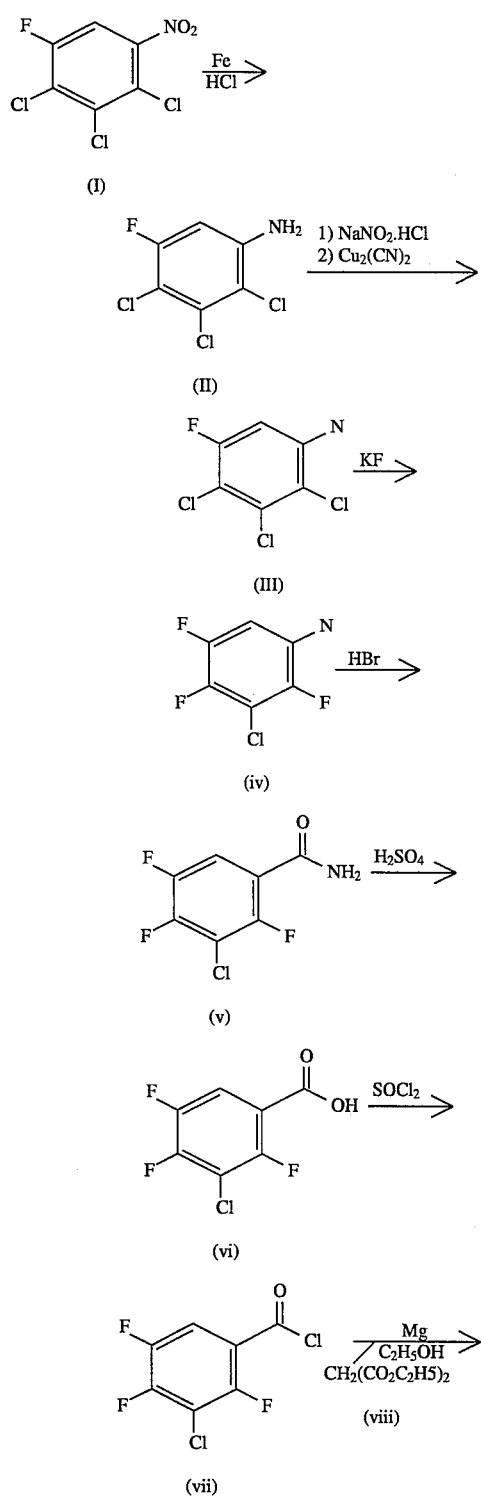
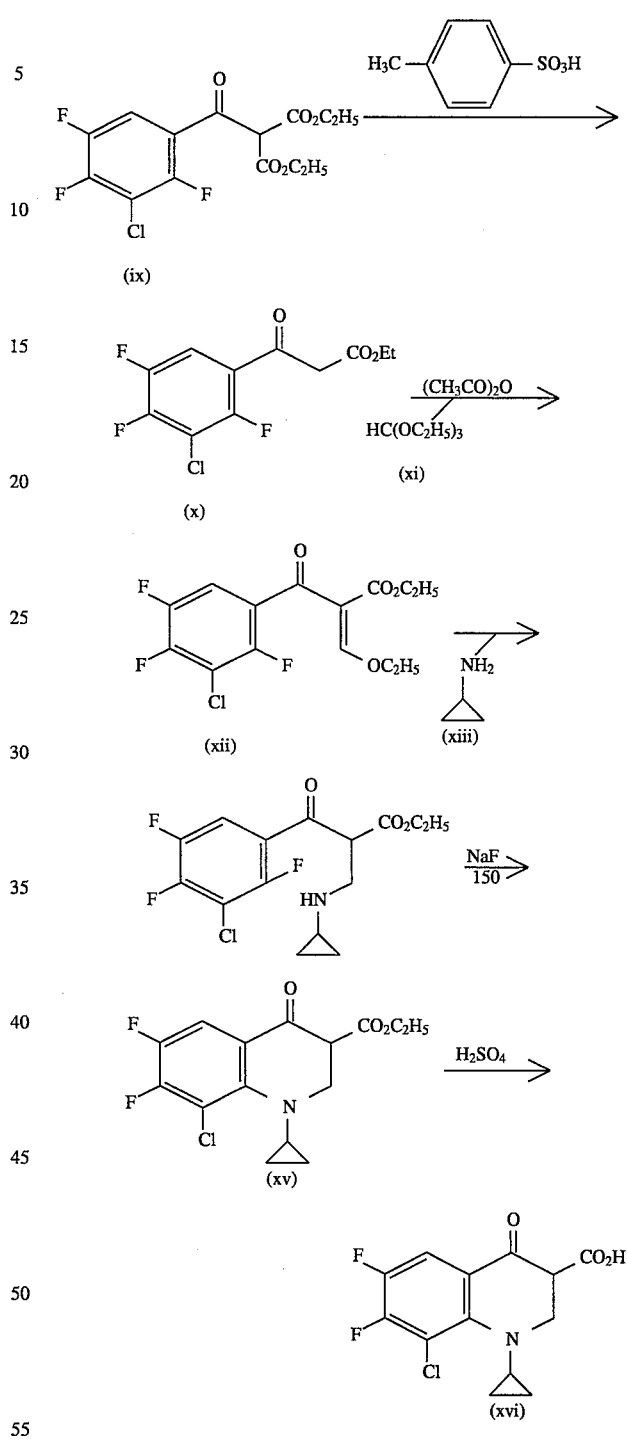
The reduction of 2,3,4-trichloro-5-fluoronitrobenzene (i) with Fe—HCl in hot water gives 2,3,4-trichloro-5-fluoroaniline (ii), which, by diazotization with NaNO₂—HCl and reaction with sodium tetra-fluoroborate and cuprous cyanide, is converted to 2,3,4-trichloro-5-fluorobenzonitrile (iii). The reaction of (iii) with KF in DMSO at 140° affords 3-chloro-2,4,5-trifluorobenzonitrile (iv), which, by hydrolysis with 30% HBr in refluxing acetic acid, gives 3-chloro-2,4,5-trifluorobenzamide (v). The hydrolysis of (v) with 18N $H_2SO_4$ at 135° yields the corrsponding benzoic acid (vi), which is treated with refluxing $SOCl_2$ to afford the acyl chloride (vii). The condensation of (vii) with diethyl malonate (viii) by means of Mg-ethanol in hot toluene gives diethyl 3-chloro-2,4,5-trifluorobenzoylmalonate (ix), which is partially decarboxylated with p-toluenesulfonic acid in refluxing water to give ethyl 3-chloro- 2,4,5-trifluorobenzoylacetate (x). The condensation of (x) with triethyl orthoformate (xi) in refluxing acetic anhydride yields ethyl 2-(3-chloro-2,4,5-trifluorobenzoyl)-3-ethoxyacrylate (xii), which is treated with cyclopropylamine (xiii) in ethanol to afford ethyl 2-(3-chloro-2,4,5-trifluorobenzoyl)-3-(cyclopropylamino)acrylate (xiv). The cyclization of (xiv) by means of NaF in DMF at 150° gives ethyl 8-chloro-1-cyclopropyl-6,7-difluoro-4-oxo-1,4-dihydroquinoline-3-carboxylate (xv), which is hydrolyzed with $H_2SO_4$ in refluxing water-acetic acid to the corresponding carboxylic acid (xvi).

One of the compounds of formula (IV) can be prepared by the condensation of ethyl ethoxymagnesium malonate with 2,3,4,5-tetrafluorobenzoyl chloride (accessible from the corresponding carboxylic acids), followed by hydrolysis of the condensate [*Chem. Pharm. Bull.* 34(10) 4098 (1986)].

The compound of formula (I) can be converted into their pharmaceutically acceptable salts by employing conventional methods. For example, the compound of formula (I) can be converted into the salt with an inorganic acid such as hydrochloric, sulfuric and phosphoric acids, or an organic acid such as methanesulfonic, lactic, oxalic and acetic acids, or a salt of an alkaline metal such as sodium and potassium.

The following examples are intended to further illustrate the present invention, without limiting the scope of the invention.

EXAMPLE 1

Preparation of 1-cyclopropyl-6,8-difluoro-7-[(2,8 diazabicyclo[4.3.0.]non-5-en)-8-yl]-1,4-dihydroquinoline-4-oxo- 3-carboxylic Acid 1.43 g of 1-cyclopropyl-6,7,8-trifluoro-1,4-dihydroquinoline-4-oxo-3-carboxylic acid and 0.96 g of 2,8-diazabicyclo[4.3.0.]non-5-ene dihydrochloride were suspended in 10 ml of acetonitrile and then 3 ml of 1,8-diazabicyclo[5.4.0] undec-7-ene was added thereto. The resulting mixture was heated at 60° C. for 4 hours, and then cooled to room temperature. The resulting white solid was filtered, washed twice with chilled acetonitrile, and then dried to obtain 1.8 g of the desired compounds.

$^1$H-NMR (CDCl$_3$, δ): 1.15(4H, m), 2.10(1H, m), 2.30(1H, m), 2.95(1H, m), 3.25(1H, m), 3.60(1H, m), 3.85(1H, m), 4.00(3H, m), 5.66(1H, m), 7.80(1H, d), 8.65(1H, s)

EXAMPLE 2

Preparation of 1-cyclopropyl-6-fluoro-8-chloro-7-[2,8-diazabicyclo[4.3.0]non-5-en)-8-yl]-1,4-dihydroquinoline-4-oxo-3-carboxylic Acid 1.50 g of 1-cyclopropyl-6,7-difluoro-8-chloro-1,4-dihydroquinoline-4-oxo-3-carboxylic acid and 0.97 g of 2,8-diazabicyclo[4.3.0]non-5-ene dihydrochloride were dissolved in 10 ml of dimethylformamide, and then 4 ml of pyridine was added thereto. The reaction mixture was heated at 100° C. for 6 hours. The reaction solvent was removed under reduced pressure at below 40° C. and the residue was washed with water, then with chilled acetonitrile, and dried to obtain 1.2 g of the desired compound as a white solid.

$^1$H-NMR (CDCl$_3$, δ): 1.20(4H, m), 2.10(1H, m), 2.30(1H, m), 2.65~4.15(7H, m), 4.95(1H, m), 5.10(1H, m), 5.60(1H, m), 7.56(1H, d), 8.61(1H, s)

EXAMPLE 3

Preparation of 1-cyclopropyl-6-fluoro-8-methoxy-7-[(2,8-diazabicyclo[4.3.0]non-5-en)-8-yl]-1,4-dihydroquinoline-4-oxo-3-carboxylic Acid 1.47 g of 1-cyclopropyl-6,7-difluoro-8-methoxy-1,4-dihydroquinoline-4-oxo-3-carboxylic acid and 0.97 g of 2,8-diazabicyclo[4.3.0]non-5-ene dihydrochloride were subjected to the same process as described in Example 1 to obtain 1.31 g of the desired compound.

$^1$H-NMR (CDCl$_3$, δ): 1.16(4H, m), 2.11(1H, m), 2.70~4.15(7H, m), 4.02(3H, s), 4.65(1H, d), 5.70(1H, s), 7.84(1H, d), 8.80(1H, s)

EXAMPLE 4

Preparation of 1-cyclopropyl-6-fluoro-7-[2,8-diazabicyclo [4.3.0]non-5-en)-8-yl]-1,4-dihydroquinoline-4-oxo-3-carboxylic Acid 1.32 g of 1-cyclopropyl-6,7-difluoro-1,4-dihydroquinoline-4-oxo-3-carboxylic acid and 0.97 g of 2,8-diazabicyclo[4.3.0]non-5-ene dihydrochloride were subjected to the same process as described in Example 1 to obtain 1.56 g of the desired compound.

$^1$H-NMR (CDCl$_3$, δ): 1.15(4H, m), 2.23(1H, m), 2.32(1H, m), 2.95(1H, m), 3.25(1H, m), 3.60(1H, m), 3.81(1H, m), 4.0(3H, m), 4.65(1H, d), 5.75(1H, s), 6.99(1H, d), 7.82(1H, d), 8.62(1H, s)

EXAMPLE 5

Preparation of 1-cyclopropyl-6-fluoro-8-methyl-7-[(2,8-diazabicyclo[4.3.0]non-5-en)-8-yl]-1,4-dihydroquinoline-4-oxo-3-carboxylic Acid 1.40 g of 1-cyclopropyl-6,7-difluoro-8-methyl-1,4-dihydroquinoline-4-oxo-3-carboxylic acid and 0.97 g of 2,8-diazabicyclo[4.3.0]-non-5-ene dihydrochloride were suspended in 15 ml of acetonitrile, and then 4 g of 1,8-diazabicyclo[5.4.0]undec-7-ene was added thereto. The resulting mixture was heated under reflux for 10 hours. The reaction solvent was evaporated under reduced pressure, and the residue was suspended in water, stirred and filtered. The resulting solid was treated with aqueous sodium bicarbonate solution to dissolve the solid, and then adjusted to pH 2 with 10% hydrochloric acid to obtain the pure solid product. The resulting solid was filtered, and then evaporated under reduced pressure to obtain 0.87 g of the desired compound as a white solid.

$^1$H-NMR (CDCl$_3$, δ): 1.15(4H, m), 2.10(1H, m), 2.3(3H, s), 2.70~4.16(7H, m), 4.95(1H, m), 5.10(1H, m), 5.62(1H, m), 7.61(1H, d), 8.61(1H, s)

EXAMPLE 6

Preparation of
1-cyclopropyl-5-amino-6,8-difluoro-7-[(2,8-diazabicyclo[4.3.0]non-5-en)-8-yl]-1,4-dihydroquinoline-4-oxo-3-carboxylic Acid 1.50 g of 1-cyclopropyl-5-amino-6,7,8-trifluoro-1,4-dihydroquinoline-4-oxo-3-carboxylic acid and 0.98 g of 2,8-diazabicyclo[4.3.0]non-5-ene dihydrochloride were subjected to the same process as described in Example 1 to obtain 1.60 g of the desired compound.

$^1$H-NMR (CDCl$_3$, δ): 1.15(4H, m), 2.12(1H, m), 2.30(1H, m), 2.95(1H, m), 3.25~4.0(6H, m), 4.65(1H, d), 5.75(1H, s), 8.92(1H, s)

EXAMPLE 7

Preparation of
1-cyclopropyl-6-fluoro-7-[(2,8-diazabicyclo[4.3.0.]non-5-en)-8-yl]-4-oxo-1,8-naphthyridine-3-carboxylic Acid 1.41 g of 1-cyclopropyl-6,7-difluoro-4-oxo-1,8-naphthyridine-3-carboxylic acid and 0.97 g of 2,8-diazabicyclo[4.3.0]non-5-ene dihydrochloride were subjected to the same process as described in Example 1 to obtain 1.87 g of the desired compound.

$^1$H-NMR (CDCl$_3$+d$_6$-DMSO, δ): 1.15(4H, m), 2.23(1H, m), 2.32(1H, m), 2.95(1H, m), 3.25(1H, m), 3.60(1H, m), 3.81(1H, m), 4.0(3H, m), 4.65(1H, d), 5.75(1H, s), 7.99(1H, d), 8.71(1H, s)

EXAMPLE 8

Preparation of
1-ethyl-6fluoro-7-[(2,8-diazabicyclo[4.3.0]non-5-en)-8-yl]-1,4-dihydroquinoline-4-oxo-3-carboxylic Acid 1.26 g of 1-ethyl-6,7-difluoro-1,4-dihydroquinoline-4-oxo-3-carboxylic acid and 9.80 g of 2,8-diazabicyclo[4.3.0]non-5-ene dihydrochloride were subjected to the same process as described in Example 1 to obtain 1.43 g of the desired compound.

$^1$H-NMR (CDCl$_3$, δ): 1.26(3H, t), 2.12(1H, m), 2.30~4.15(10H, m), 4.95(1H, m), 4.0(2H, m), 5.10(1H, m), 5.60(1H, m), 7.01(1H, d), 7.51(1H, d), 8.68(1H, s)

EXAMPLE 9

Preparation of
1-(2,4-difluorophenyl)-6-fluoro-7-[(2,8-diazabicyclo[4.3.0]non-5-en)-8-yl]-4-oxo-1,8-naphthyridine-3-carboxylic Acid 1.20 g of 1-(2,4)-difluorophenyl)-6,7-difluoro-4-oxo-1,8-naphthyridine-3-carboxylic acid and 0.65 g of 2,8-diazabicyclo[4.3.0]non-5-ene dihydrochloride were subjected to the same process as described in Example 2 to obtain 1.31 g of the desired compound.

$^1$H-NMR (CDCl$_3$, δ): 1.17(4H, m), 2.12(1H, m), 2.29(1H, m), 2.36(1H, m), 3.25(1H, m), 3.60(1H, m), 3.39(1H, m), 4.0(3H, m), 4.71(1H, d), 5.75(1H, s), 7.45(1H, m), 7.73(1H, m), 7.94(1H, m), 7.95(1H, d), 8.80(1H, s)

EXAMPLE 10

Preparation of
1-cyclopropyl-6,8-difluoro-7-[(2-methyl-2,8-diazabicyclo[4.3.0]non-5-en)-8-yl]-1,4-dihydroquinoline-4-oxo-3-carboxylic Acid 1.42 g of 1-cyclopropyl-6,7,8-trifluoro-1,4-dihydroquinoline-4-oxo-3-carboxylic acid and 1.05 g of 2-methyl-2,8-diazabicyclo[4.3.0]non-5-ene dihydrochloride were subjected to the same process as described in Example 1 to obtain 1.96 g of the desired compound.

$^1$H-NMR (CDCl$_3$, δ): 1.15(4H, m), 2.10~4.15(12H, m), 4.95(1H, m), 5.10(1H, m), 7.78(1H, d), 8.71(1H, s)

EXAMPLE 11

Preparation of
1-cyclopropyl-6-fluoro-8-chloro-7-[(2-methyl-2,8-diazabicyclo[4.3.0]non-5-en)-8-yl]-1,4-dihydroquinoline-4-oxo-3-carboxylic Acid 1.50 g of 1-cyclopropyl-6,7-difluoro-8-chloro-1,4-dihydroquinoline-4-oxo-3-carboxylic acid and 1.04 g of 2-methyl-2,8-diazabicyclo[4.3.0]non-5-ene dihydrochloride were subjected to the same process as described in Example 1 to obtain 1.96 g of the desired compound.

$^1$H-NMR (CDCl$_3$, δ): 1.08(4H, m), 2.10~2.30(5H, m), 2.95(1H, m), 3.25(1H, m), 3.60(1H, m), 3.85(1H, m), 4.0(3H, m), 4.65(1H, d), 7.54(1H, d), 8.64(1H, s)

EXAMPLE 12

Preparation of
1-cyclopropyl-6-fluoro-8-methoxy-7-[(2-methyl-2,8-diazabicyclo[4.3.0]non-5-en)-8-yl]-1,4-dihydroquinoline-4-oxo-3-carboxylic Acid 1.48 g of 1-cyclopropyl-6,7-difluoro-8-methoxy-1,4-dihydroquinoline-4-oxo-3-carboxylic acid and 1.04 g of 2-methyl-2,8-diazabicyclo[4.3.0]non-5-ene dihydrochloride were subjected to the same process as described in Example 1 to obtain 2.16 g of the desired compound.

$^1$H-NMR (CDCl$_3$, δ): 1.15(4H, m), 2.11(1H, m), 2.30(1H, m), 2.95(1H, m), 3.25(1H, m), 3.60(1H, m), 3.85(1H, m), 4.0(3H, m), 4.10(3H, s), 4.65(1H, d), 7.86(1H, d), 8.84(1H, s)

EXAMPLE 13

Preparation of
1-cyclopropyl-5-amino-6,8-difluoro-7-[(2-methyl-2,8-diazabicyclo[4.3.0]non-5-en)-8-yl]-1,4-dihydroquinoline-4-oxo-3-carboxylic Acid 1.50 g of 1-cyclopropyl-5-amino-6,7,8-trifluoro-1,4-dihydroquinoline-4-oxo-3-carboxylic acid and 1.04 g of 2-methyl-2,8-diazabicyclo[4.3.0]non-5-ene dihydrochloride were subjected to the same process as described in Example 1 to obtain 2.06 g of the desired compound.

$^1$H-NMR (CDCl$_3$, δ): 1.15(4H, m), 2.12~2.30(5H, m), 2.95(1H, m), 3.25~4.0(6H, m), 4.68(1H, d), 8.94(1H, s)

EXAMPLE 14

Preparation of
1-cyclopropyl-6-fluoro-7-[(2-methyl-2,8-diazabicyclo[4.3.0]non-5-en)-8-yl]-1,8-dihydronaphthyridine-3-carboxylic Acid 1.41 g of 1-cyclopropyl-6-fluoro-7-chloro-1,8-dihydronaphthyridine-3-carboxylic acid and 1.04 g of 2-methyl-2,8-diazabicyclo[4.3.0]non-5-ene dihydrochloride were subjected to the same process as described in Example 1 to obtain 1.91 g of the desired compound.

$^1$H-NMR (CDCl$_3$, δ): 1.15(4H, m), 2.12~2.30(5H, m), 2.95(1H, m), 3.25~4.0(6H, m), 4.68(1H, d), 7.85(1H, d), 8.68(1H, s)

EXAMPLE 15

Preparation of
1-cyclopropyl-6,8-difluoro-7-[(3-methyl-2,8-diazabicyclo[4.3.0]non-5-en)-8-yl]-1,4-dihydroquinoline-4-oxo-3-carboxylic Acid 1.41 g of 1-cyclopropyl-6,7,8-trifluoro-1,4-dihydroquinoline-4-oxo-3-carboxylic acid and 1.04 g of 3-methyl-2,8-diazabicyclo[4.3.0]non-5-ene dihydrochloride were subjected to the same process as described in Example 1 to obtain 2.20 g of the desired compound.

$^1$H-NMR (CDCl$_3$, δ): 1.15~1.27(7H, m), 2.16~2.36(2H, m), 2.95(1H, m), 3.25~4.10(6H, m), 5.52(1H, m), 7.78(1H, d), 8.76(1H, s)

EXAMPLE 16

Preparation of
1-cyclopropyl-6-fluoro-8-chloro-7-[(3-methyl-2,8-diazabicyclo[4.3.0]non-5-en)-8-yl]-1,4-dihydroquinoline-4-oxo-3-carboxylic Acid 1.50 g of 1-cyclopropyl-6,7-difluoro-8-chloro-1,4-dihydroquinoline-4-oxo-3-carboxylic acid and 1.04 g of 3-methyl-2,8-diazabicyclo[4.3.0]non-5-ene dihydrochloride were subjected to the same process as described in Example 1 to obtain 1.83 g of the desired compound.

$^1$H-NMR (CDCl$_3$, δ): 1.16~1.22(4H, m), 2.08~4.16(9H, m), 4.95(1H, m), 5.49(1H, m), 7.81(1H, d), 8.78(1H, s)

EXAMPLE 17

Preparation of
1-cyclopropyl-6-fluoro-8-methoxy-7-[(3-methyl-2,8-diazabicyclo[4.3.0]non-5-en)-8-yl]-1,4-dihydroquinoline-4-oxo- 3-carboxylic Acid 1.48 g of 1-cyclopropyl-6,7-difluoro-8-methoxy-1,4-dihydroquinoline-4-oxo-3-carboxylic acid and 1.04 g of 3-methyl-2,8-diazabicyclo[4.3.0]non-5-ene dihydrochloride were subjected to the same process as described in Example 1 to obtain 1.91 g of the desired compound.

$^1$H-NMR (CDCl$_3$, δ): 1.16~1.25(4H, m), 2.10~4.16(9H, m), 4.05(3H, s), 4.95(1H, m), 5.49(1H, m), 7.89(1H, d), 8.81(1H, s)

EXAMPLE 18

Preparation of
1-cyclopropyl-5-amino-6,8-difluoro-7-[3-methyl-2,8-diazabicyclo[4.3.0]non-5-en)-8-yl]-1,4-dihydroquinoline-4-oxo- 3-carboxylic Acid 1.50 g of 1-cyclopropyl-5-amino-6,7,8-trifluoro-1,4-dihydroquinoline-4-oxo-3-carboxylic acid and 1.04 g of 3-methyl-2,8-diazabicyclo[4.3.0]non-5-ene dihydrochloride were subjected to the sampe process as described in Example 1 to obtain 1.68 g of the desired compound.

$^1$H-NMR (CDCl$_3$, δ): 1.14~1.21(7H, m), 2.10~4.10(9H, m), 4.95(1H, m), 5.56(1H, m), 8.76(1H, s)

EXAMPLE 19

Preparation of
1-cyclopropyl-6,8-difluoro-7-[(5-methyl-2,8-diazabicyclo[4.3.0]non-5-en)-8-yl]-dihydroquinoline-4-oxo-3-carboxylic Acid 1.42 g of 1-cyclopropyl-6,7,8-trifluoro-1,4-dihydroquinoline-4-oxo-3-carboxylic acid and 1.04 g of 5-methyl-2,8-diazabicyclo[4.3.0]non-5-ene dihydrochloride were subjected to the same process as described in Example 1 to obtain 1.69 g of the desired compound.

$^1$H-NMR (CDCl$_3$, δ): 1.15(4H, m), 2.23~2.35(5H, m), 2.95(1H, m), 3.25(1H, m), 3.60(1H, m), 3.81(1H, m), 4.0(3H, m), 4.65(1H, d), 5.75(1H, s), 7.80(1H, d), 8.71(1H, s)

EXAMPLE 20

Preparation of
1-cyanopropyl-6-fluoro-8-chloro-7-[(5-methyl-2,8-diazabicyclo[4.3.0]non-5-en)-8-yl]-1,4-dihydroquinoline-4-oxo-3-carboxylic Acid 1.50 g of 1-cyclopropyl-6,7-difluoro-8-chloro-1,4-dihydroquinoline-4-oxo-3-carboxylic acid and 1.04 g of 5-methyl-2,8-diazabicyclo[4.3.0]non-5-ene dihydrochloride were subjected to the sampe process as described in Example 1 to obtain 1.87 g of the desired compound.

$^1$H-NMR (CDCl$_3$, δ): 1.14(4H, m), 2.10~4.12(12H, m), 4.95(1H, m), 5.10(1H, m), 5.62(1H, m), 7.81(1H, d), 8.81(1H, s)

EXAMPLE 21

Preparation of
1-cyclopropyl-6,8-difluoro-7-[(2,8-diazabicyclo[4.3.0]non-5-en)-8-yl]-1,4-dihydroquinoline-4-oxo-3-carboxylic Acid Hydrochloride 0.388 g of 1-cyclopropyl-6,8-difluoro-7-[(2,8-diazabicyclo[4.3.0]non-5-en)-8-yl]- 1,4-dihydroquinoline-4-oxo-3-carboxylic acid obtained from Example 1 was dissolved in methanol saturated with hydrogen chloride, and the reaction solution was stirred for 1 hour. The resulting solid was filtered, washed with chilled methanol, and then dried to obtain 0.403 g of the desired compound as a light yellow solid.

$^1$H-NMR (d$_6$-DMSO, δ): 1.16(4H, m), 2.21~4.06(9H, m), 4.65(1H, d), 5.75(1H, s), 7.81(1H, d), 8.81(1H, s)

EXAMPLE 22

Preparation of
1-cyclopropyl-6-fluoro-8-chloro-7-[(2,8-diazabicylo[4.3.0]non-5-en)-8-yl]-1,4-dihydroquinoline-4-oxo-3-carboxylic Acid Lactate 0.404 g of 1-cyclopropyl-6-fluoro-8-chloro-7-[(2,8-diazabicyclo[4.3.0]non-5-en- 8-yl]-1,4-dihydroquinoline-4-oxo-3-carboxylic acid obtained from Example 2 was dissolved in 5 ml of mixture of chloroform-methanol (5:1, v/v), and then 0.09 g of lactic acid was added thereto. The resulting reaction solution was stirred for 4 hours, evaporated under reduced pressure, washed twice with acetonitrile, and then dried under reduced pressure to obtain 0.40 g of the desired compound.

$^1$H-NMR (CD$_3$OD, δ): 1.14(1H, m), 2.20–4.06(11H, m), 4.65(1H, d), 5.75(1H, s), 7.81(1H, d), 8.81(1H, s)

EXAMPLE 23

Preparation of
1-cyclopropyl-6-fluoro-8-methoxy-7-[(5-methyl-2,8-diazabicyclo[4.3.0]non-5-en)-8-yl]-1,4-dihydroquinoline-4-oxo- 3-carboxylic Acid Step (1): Preparation of Ethyl{2,5-difluoro-3-methoxy-4-[(5-methyl-2,8-diazabicylo[ 4.3.0]non-5-en)-8-yl}benzoyl Acetate 1.06 g of ethyl(2,4,5-trifluoro-3-methoxy)benzoyl acetate, 0.91 g of 5-methyl- 2,8-diazabicyclo[4.3.0]non-5-ene and 1 g of calcium carbonate were added to 10 ml of acetonitrile and the resulting solution was heated at 60° C. for 6 hours. The solvent was evaporated under reduced pressure and the residue was suspended in ethyl acetate, and then washed with water. The solvent was evaporated again under reduced pressure. The residue was purified on a silica gel column chromatography using hexane:ethyl acetate (3:1, v/v) to obtain 1.36 g of the desired compoumnd.

Steps (2) and (3): Preparation of 1-cyclopropyl-6-fluoro-8-methoxy-7-[(5-methyl- 2,8-diazabicyclo[4.3.0]non-5-en)-8-yl]-1,4-dihydroquinoline- 4-oxo-3-carboxylic Acid Ethyl Ester 1.16 g of benzoyl acetate obtained from the above step (1) was dissolved in 10 ml of acetate anhydride, and then 2 g of triethyl carbonate was added thereto. The resulting mixture was heated for 1 hour. After being cooled to room temperature the reaction mixture was poured into 100 ml of ice water. The reaction product was extracted with ethyl acetate, dried over magnesium sulfate, and then evaporated under reduced pressure. The residue was dissolved in ethanol, and 0.51 g of cyclopropylamine was added thereto, and then stirred at room temperature for 3 hours. The reaction mixture was then evaporated under reduced pressure, and the residue was dissolved in 5 ml of dimethylsulfoxide. 3 g of calcium fluoride was added to the resulting solution, and then heated at 60° C. for 1 hour. The reaction mixture was poured into 50 ml of ice water and the reaction product was extracted with ethyl acetate. The extract was dried over magnesium sulfate and then evaporated under reduced pressure. The resulting residue was purified on a silica gel column chromatography using hexane:ethyl acetate (5:1, v/v) to obtain 0.78 g of the desired compound.

Step (4): Preparation of 1-cyclopropyl-6-fluoro-8-methoxy-7-[(5-methyl- 2,8-diazabicyclo[4.3.0]non-5-en)-8-yl]-1,4-dihydroquinoline-4-oxo- 3-carboxylic Acid 0.71 g of the ester derivative obtained from the above steps (2) and (3) was suspended in 10 ml of 6N hydrochloric acid, and then heated under reflux for 8 hours. The solvent was evaporated under reduced pressure, and the residue was treated with an queous saturated sodium carbonate solution to remove the insoluble material. The resulting solution was washed twice with ethyl acetate, adjusted to pH 3 with 2N hydrochloric acid, and then cooled in an ice water bath to produce white solid which was filtered and then dried under reduced pressure to obtain 0.46 g of the desired compound.

$^1$H-NMR (CDCl$_3$, δ): 1.16(4H, m), 2.11(1H, m), 2.70–4.16(10H, m), 4.02(3H, s), 4.65(1H, d), 5.70(1H, d), 7.84(1H, d), 8.80(1H, s)

EXAMPLE 24

Preparation of
1-cyclopropyl-5-methyl-6-fluoro-7-[(2,8-diazabicyclo[4.3.0]non-5-en)-8-yl]-1,4-dihydroquinoline-4-oxo-3-carboxylic Acid 1.39 g of 1-cyclopropyl-5-methyl-6,7-difluoro-1,4-dihydroquinoline-4-oxo-3-carboxylic acid and 1.04 g of 2,8-diazabicyclo[4.3.0]non-5-ene dihydrochloride were subjected to the same process as described in Example 1 to obtain 1.67 g of the desired compound.

$^1$H-NMR (CDCl$_3$, δ): 1.14(4H, m), 2.10–2.30(5H, m), 2.65–4.15(7H, m), 4.95(1H, m), 5.60(1H, m), 7.71(1H, d), 8.69(1H, s)

EXAMPLE 25

Preparation of
1-cyclopropyl-6,8-difluoro-7-[(3-hydroxymethyl-2,8-diazabicyclo[4.3.0]non-5-en)-8-yl]-1,4-dihydroquinoline-4-oxo- 3-carboxylic Acid 1.43 g of 1-cyclopropyl-6,7,8-trifluoro-1,4-dihydroquinoline-4-oxo-3-carboxylic acid and 1.13 g of 3-hydroxymethyl-2,8-diazabicyclo[4,3,0]non-5-ene dihydrochloride were subjected to the same process as described in Example 1 to obtain 1.38 g of the desired compound.

$^1$H-NMR (CDCl$_3$, δ): 1.15(4H, m, 2.10–2.31(2H, m), 2.76–3.25(5H, m), 4.0(3H, m), 5.62(1H, m), 7.82(1H, d), 8.67(1H, s)

EXAMPLE 26

Preparation of
1-cyclopropyl-6,8-difluoro-7-[(3-aminomethyl-2,8-diazabicyclo[4.3.0]non-5-en)-8-yl]-1,4-dihydroquinoline-4-oxo- 3-carboxylic Acid 1.43 g of 1-cyclopropyl-6,7,8-trifluoro-1,4-dihydroquinoline-4-oxo-3-carboxylic acid and 1.20 g of 3-aminomethyl-2,8-diazabicyclo[4,3,0]non-5-ene dihydrochloride were subjected to the same process as described in Example 1 to obtain 1.52 g of the desired compound.

$^1$H-NMR (CDCl$_3$, δ): 1.14(4H, m), 2.14–2.31(2H, m), 2.76–3.18(7H, m), 4.0(1H, m), 5.61(1H, m), 7.80(1H, d), 8.71(1H, s)

EXAMPLE 27

Preparation of
1-cyclopropyl-5-amino-7-[(5-fluoro-2,8-diazabicyclo[4.3.0]non-5-en)-8-yl]-6,8-difluoro-1,4-dihydroquinoline-4-oxo-3-carboxylic Acid 1.49 g of 1-cyclopropyl-5-amino-6,7,8-trifluoro-1,4-dihydroquinoline-4-oxo-3-carboxylic acid and 1.06 g of 5-fluoro-2,8-diazabicyclo[4.3.0]non-5-ene dihydrochloride were subjected to the same process as described in Example 1 to obtain 1.87 g of the desired compound.

$^1$H-NMR (CDCl$_3$, δ): 1.14(4H, m), 2.10~2.30(2H, m), 2.95~3.25(4H, m), 3.90~ 4.00(4H, m), 8.71(1H, s)

EXAMPLE 28

Preparation of
1-cyclopropyl-5,8-dichloro-6-fluoro-7-[(2,8-diazabicyclo[4.3.0]non-5-en)-8-yl]-1,4-dihydroquinoline-4-oxo-3-carboxylic Acid 1.67 g of 1-cyclopropyl-5,8-dichloro-6,7-difluoro-1,4-dihydroquinoline-4-oxo- 3-carboxylic acid and 0.98 g of 2,8-diazabicyclo[4,3,0]non-5-ene dihydrochloride were subjected to the same process as described in Example 1 to obtain 1.42 g of the desired compound.

$^1$H-NMR (CDCl$_3$, δ): 1.15(4H, m), 2.10(1H, m), 2.30(1H, m), 2.91~3.25 (4H, m), 3.90(1H, m), 4.00(3H, m), 5.60(1H, m), 8.65(1H, s)

EXAMPLE 29

Preparation of
1-(2-fluorocyclopropyl)-6-fluoro-8-chloro-7-[(2,8-diazabicyclo[4.3.0]non-5-en)-8-yl]-1,4-dihydroquinoline-4-oxo-3-carboxylic Acid 1.58 g of 1-(2-fluorocyclopropyl)-6,7-difluoro-8-chloro-1,4-dihydroquinoline- 4-oxo-3-carboxylic acid and 0.98 g of 2,8-diazabicylo[4.3.0]non-5-ene dihydrochloride were subjected to the same process as described in Example 1 to obtain 1.21 g of the desired compound.

$^1$H-NMR (CDCl$_3$, δ): 1.18(2H, m), 2.12(1H, m), 2.30(1H, m), 2.95(1H, m), 3.25(1H, m), 3.90~4.00(7H, m), 5.62(1H, m), 8.72(1H, s)

1) Preparation of 2,8-diazabicyclo[4.3.0]non-5-ene Dihydrochloride (1) Preparation of 1-benzyl-3-carboethoxy-4-benzylaminopyrrolidine 24.7 g of 1-benzyl-3-carboethoxy-4-pyrrolidone and 10.7 g of benzylamine were added to 100 ml of benzene, and then dehydrated with Dean-Stark distillation apparatus. The residual benzene was evaporated. The residue was dissolved in 200 ml of tetrahydrofuran, and then a small amount of methyl orange was added. To this was added methanol saturated with hydrogen chloride to adjust the pH to about 4, and then 7 g of sodium cyanoborohydride was added thereto. A solution of methanol saturated with hydrogen chloride was added dropwise to the reaction solution with stirring until the pink-color of the solution did not disappear. The reaction solution was basified with 15% aqueous caustic soda solution, and then the reaction mixture was diluted with ether, after which the aqueous layer was separated the aqueous layer was removed by addition of ether. The organic layer was dried over anhydrous magnesium sulfate, evaporated under reduced pressure, and then subjected to silica gel column chromatography (hexane:ethyl acetate, 5:1 (v/v)) to obtain 24 g of the desired compound (yield: 71%).

$^1$H-NMR (CDCl$_3$, δ): 1.27(3H, t), 2.6~3.0(5H, m), 3.57(1H, m), 3.63 (2H, d), 3.80(2H, s), 4.18(2H, q), 7.31(10H, m)

(2) Preparation of N,N'-dibenzyl-2,8-diazabicyclo[4.3.0]non-5-one 33.8 g of 1-benzyl-3-carboethoxy-4-benzylaminopyrrolidine and 50 ml of ethyl acrylate were added to 100 ml of ethanol, and then refluxed with stirring for 3 days. The ethanol and ethyl acrylate were removed under reduced pressure. The residue was dissolved in 100 ml of toluene, and then the reaction mixture was cooled in an ice water bath. 8 g of potassium t-butoxide was added thereto, and then stirred at room temperature over night. 100 ml of water was added to the reaction mixture, and then stirred well. The aqueous layer was separated, and then neutralized with concentrated sulfuric acid. The aqueous layer was extracted three times with ethyl acetate, and the solvent was then evaporated under reduced pressure. To the residue was added 100 ml of concentrated hydrochloric acid, and the resulting solution was stirred under reflux for 4 hours. The reaction solution was concentrated to a volume of 50 ml under reduced pressure, neutralized with 1N NaOH solution, extracted twice with ethyl acetate, and then dried over anhydrous magnesium sulfate. The solvent was evaporated under reduced pressure, and then purified on a silica gel column chromatography (hexane:ethyl acetate, 3:1 (v/v)) to obtain 17.1 g of the desired compound (yield: 53.4%).

$^1$H-NMR (CDCl$_3$, δ): 2.3~3.0(9H, m), 3.20~3.70(2H, ABq), 3.50(2H, s), 3.40(1H, q), 7.15(10H, m)

(3) Preparation of N,N'-dibenzyl-2,8-diazabicyclo[4.3.0]non-5-ol

To a suspension of 4.0 g of NaBH$_4$ in 100 ml of ethanol was added dropwise a solution of 32.0 of N,N'-dibenzyl-2,8-diazabicyclo[4.3.0]non-5-one in 100 ml of ethanol. After the reaction mixture was stirred at room temperature for 3 hours, 20 ml of 15% NaOH was added thereto, and then filtered. The filtrate was evaporated under reduced pressure, extracted with ethyl acetate, dried over anhydrous magnesium sulfate, and then evaporated under reduced pressure to obtain the desired compound in a quantitative yield as a light yellow syrup.

$^1$H-NMR (CDCl$_3$, δ): 1.60~3.00(11H, m), 3.20~3.60(3H, m), 3.70(2H, d), 3.90(1H, m), 7.30(10H, m)

(4) Preparation of N,N'-di-t-butoxycarbonyl-2,8-diazabicyclo[4.3.0]non-5-ol 32.2 g of N,N'-dibenzyl-2,8-diazabicyclo[4.3.0]non-5-ol was added to 250 ml of methanol containing 10 ml of formic acid together with 3 g of 10% Pd/C, then agitated under hydrogen gas (initial pressure of 60 psi). After the reaction was completed, the reaction solution was filtered through celite, neutralized with saturated sodium bicarbonate solution, and then stirred for 14 hours after an addition of 40 g of di-tert-butyl-dicarbonate. The reaction solution was evaporated under reduced pressure, and the residue was purified on a silica gel column chromatography (hexane:ethyl acetate, 5:1 (v/v)) to obtain 30.78 g of the desired compound (yield: 90%).

$^1$H-NMR (CDCl$_3$, δ): 1.50(8H, s), 1.70~2.00(2H, m), 2.20(1H, m), 2.50 (1H, m), 2.80–4.10(7H, m), 4.60(1H, m)

(5) Preparation of N,N'-di-t-butoxycarbonyl-2,8-diazabicyclo[4.3.0]non-5-ene 17.1 g of N,N'-di-t-butoxycarbonyl-2,8-diazabicyclo[4.3.0]non-5-ol and 7 ml of triethylamine were dissolved in 100 ml of methylene chloride. The reaction solution was cooled in an ice water bath, and then 4.2 ml of methanesulfonyl chloride was added dropwise thereto. The reaction mixture was stirred at room temperature for 10 hours, washed with water, dried over anhydrous magnesium sulfate, and then evaporated under reduced pressure. The residue was dissolved in 50 ml of dimethylsulfoxide, and then 10 ml of DBU was added thereto. The reaction mixture was poured into 200 ml of ice water, extracted there times with ethyl acetate and then dried over anhydrous magnesium sulfate. The solvent was evaporated under reduced pressure and subjected to a silica gel column chromatography (hexane:ethyl acetate, 6:1 (v/v)) to obtain 9.8 g of the desired compound (yield: 61%).

$^1$H-NMR (CDCl$_3$, δ): 1.46(18H, s), 2.10(1H, m), 2.70–4.20(7H, m), 5.30(1H, m), 5.80(1H, m)

(6) Preparation of 2,8-diazabicyclo[4.3.0]non-5-ene Dihydrochloride

To 30 ml of methanol saturated with hydrogen chloride gas was added 9.72 g of N,N'-di-t-butoxycarbonyl-2,8-diazabicyclo[4.3.0]non-5-ene, stirred at room temperature for 4 hours, and then evaporated under reduced pressure to obtain 5.85 g of the desired compound.

$^1$H-NMR (CD$_3$OD, δ): 2.10(1H, m), 2.70–4.20(7H, m), 5.10(1H, m), 5.60 (1H, m)

IN VITRO ANTIBACTERIAL ACTIVITY TEST

In order to demonstrate the superior antibacterial activity of the quinolone derivatives of the present invention, the minimal inhibitory concentration (MIC, μg/ml) of several compound synthesized in Examples hereof was determined in accordance with the agar culture medium two-fold dilution method (Hoechst 345) by using a Muller-Hinton agar medium. The strains having $10^7$ CFU/ml were inoculated on the culture medium, and the growth of the strains was observed after incubating them at 37° C. for 18 hours, in which ofloxacin, ciprofloxacin and spafloxacin were used as control materials. Hoechst standard strains were used as the test strains. The results of the MIC tests are shown in Tables 1 and 2.

TABLE 1

In vitro antibacterial activity test

| Strain | A | B | C | D | E | F |
| --- | --- | --- | --- | --- | --- | --- |
| Streptococcus pyogenes 308A | 0.391 | 0.195 | 0.781 | 3.125 | 3.125 | 1.563 |
| Streptococcus pyogenes 77A | 0.195 | 0.098 | 0.195 | 1.563 | 0.781 | 0.391 |
| Streptococcus faecium MD 8b | 0.195 | 0.195 | 0.195 | 0.781 | 0.781 | 0.391 |
| Staphylococcus aureus SG 511 | 0.025 | 0.013 | 0.025 | 0.391 | 0.391 | 0.049 |
| Staphylococcus aureus 285 | 0.025 | 0.013 | 0.049 | 0.391 | 0.781 | 0.098 |
| Staphylococcus aureus 503 | 0.025 | 0.013 | 0.013 | 0.391 | 0.781 | 0.025 |
| Escherichia coli O 55 | 0.004 | 0.004 | <0.002 | 0.013 | <0.002 | <0.002 |
| Escherichia coli DC 0 | 0.098 | 0.098 | 0.391 | 0.781 | 0.195 | 0.391 |
| Escherichia coli DC 2 | 0.025 | 0.013 | 0.049 | 0.195 | 0.098 | 0.049 |
| Escherichia coli TEM | 0.007 | 0.007 | 0.013 | 0.049 | 0.007 | 0.025 |
| Escherichia coli 1507E | 0.013 | 0.013 | 0.013 | 0.049 | 0.007 | 0.025 |
| Pseudomonas aeruginosa 9027 | 0.781 | 0.781 | 0.781 | 1.563 | 0.391 | 1.563 |
| Pseudomonas aeruginosa 1592E | 0.391 | 0.391 | 0.391 | 1.563 | 0.391 | 0.781 |
| Pseudomonas aeruginosa 1771 | 0.391 | 0.391 | 0.391 | 1.563 | 0.391 | 0.781 |
| Pseudomonas aeruginosa 1771M | 0.195 | 0.195 | 0.195 | 0.391 | 0.098 | 0.195 |
| Salmonella typhimurium | 0.007 | 0.004 | <0.002 | 0.049 | 0.007 | 0.013 |
| Klebsiella aerogenes 1082E | 0.004 | 0.004 | 0.025 | 0.013 | <0.002 | <0.002 |
| Klebsiella aerogenes 1552E | 0.013 | 0.013 | 0.007 | 0.098 | 0.007 | 0.049 |
| Enterobacter cloacae P 99 | 0.007 | 0.007 | <0.002 | 0.049 | 0.007 | 0.025 |
| Enterobacter cloacae 1321E | 0.004 | 0.004 | 0.004 | 0.025 | 0.004 | 0.007 |

A: The compound prepared in Example 1
B: The compound prepared in Example 2
C: The compound prepared in Example 21
D: Ofloxacin
E: Ciprofloxacin
F: Spafloxacin

TABLE 2

In vitro antibacterial activity against methicillin resistant Staphylococcus aureus

| Strain | A | B | D | E |
| --- | --- | --- | --- | --- |
| Staphylococcus aureus 88 E | 0.049 | 0.195 | 0.391 | 0.781 |
| Staphylococcus aureus 121 E | 0.098 | 0.195 | 0.391 | 0.781 |
| Staphylococcus aureus 208 E | 0.098 | 0.195 | 0.391 | 0.781 |
| Staphylococcus aureus 256 E | 0.098 | 0.195 | 0.391 | 1.563 |
| Staphylococcus aureus 690 E | 0.049 | 0.098 | 0.391 | 0.781 |
| Staphylococcus aureus 692 E | 0.049 | 0.098 | 0.391 | 0.391 |
| Staphylococcus aureus 693 E | 0.049 | 0.098 | 0.391 | 0.781 |
| Staphylococcus aureus 694 E | 0.098 | 0.195 | 0.781 | 0.781 |
| Staphylococcus aureus 695 E | 0.049 | 0.098 | 0.391 | 0.781 |
| Staphylococcus aureus 697 E | 0.049 | 0.098 | 0.195 | 0.391 |
| Staphylococcus aureus 701 E | 0.098 | 0.195 | 0.391 | 0.781 |
| Staphylococcus aureus 703 E | 0.098 | 0.195 | 0.391 | 0.781 |
| Staphylococcus aureus 705 E | 0.098 | 0.195 | 0.391 | 0.781 |
| Staphylococcus aureus 706 E | 0.098 | 0.195 | 0.391 | 0.391 |
| Staphylococcus aureus 707 E | 0.098 | 0.195 | 0.391 | 0.781 |
| Staphylococcus aureus 708 E | 0.025 | 0.049 | 0.195 | 0.195 |
| Staphylococcus aureus 711 E | 0.025 | 0.098 | 0.391 | 0.781 |
| Staphylococcus aureus 714 E | 0.049 | 0.195 | 0.391 | 0.781 |
| Staphylococcus aureus 725 E | 0.098 | 0.195 | 0.391 | 0.781 |

A: The compound prepared in Example 1
B: The compound prepared in Example 2
D: Ofloxacin
E: Ciprofloxacin

What is claimed is:

1. A quinolone carboxylic acid derivative of formula (I):

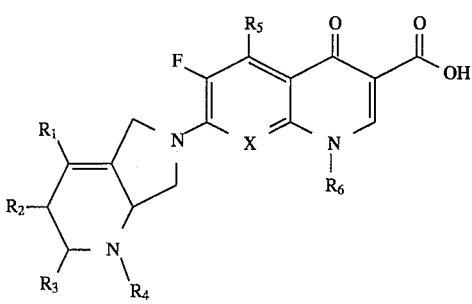

wherein,

R₁, R₂, and R₃, which may be the same or different, are each hydrogen or a halogen atom, or a lower alkyl group optionally substituted with an amino or a hydroxy group;

R₄ is hydrogen atom, a lower alkyl, benzyl, t-butoxycarbonyl or ethoxycarbonyl group;

R₅ is hydrogen, chlorine atom, methyl or an amino group;

R₆ is a lower alkyl group, or a cyclopropyl or a phenyl group optionally substituted with a halogen atom; and X is a methyne group optionally substituted with a lower alkyl, a lower alkyloxy group or a halogen atom, and pharmaceutically acceptable salts thereof.

2. The compound of claim 1 wherein the compound of formula (I) is 1-cyclopropyl-6-fluoro-8-methoxy-7-[(2,8-diazabicyclo[ 4.3.0]non-5-en)-8-yl]-1,4-dihydroquinoline-4-oxo- 3-carboxylic acid.

3. A compound of formula (VIII):

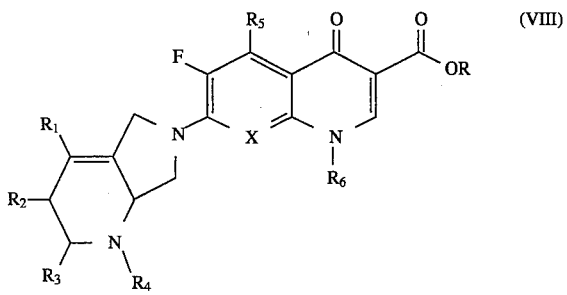

wherein,

R₁, R₂, and R₃, which may be the same or different, are each hydrogen or a halogen atom, or a lower alkyl group optionally substituted with an amino or a hydroxy group;

R₄ is hydrogen atom, a lower alkyl, benzyl, t-butoxycarbonyl or ethoxycarbonyl group;

R₅ is hydrogen, chlorine atom, methyl or an amino group;

R₆ is a lower alkyl group, or a cyclopropyl or a phenyl group optionally substituted with a halogen atom; and X is a methyne group optionally substituted with a lower alkyl, a lower alkyloxy group or a halogen atom, and R and a lower alkyl group.

4. A pharmaceutical composition comprising a compound according to claim 1 as an active antibacterial ingredient in an effective amount.

5. A method for the treatment of bacterial infection wherein a compound of claim 1 is administered to a host in need of such treatment in a therapeutically effective amount.

6. The compound of claim 1 wherein the compound of formula (I) is one of the following compounds:

1-cyclopropyl-6,8-difluoro-7-[(2,8-diazabicyclo[ 4.3.0]non-5-en)-8-yl]-1,4-dihydroquinoline-4-oxo- 3-carboxylic acid;

1-cyclopropyl-6-fluoro-8-chloro-7-[(2,8-diazabicyclo[ 4.3.0]non-5-en)-8-yl]-1,4-dihydroquinoline-4-oxo- 3-carboxylic acid;

1-(2-fluorocyclopropyl)-6-fluoro-8-chloro-7-[(2,8-diazabicyclo[ 4.3.0]non-5-en)-8-yl]-1,4-dihydroquinoline-4-oxo- 3-carboxylic acid;

1-cyclopropyl-5,8-dichloro-6-fluoro-7-[(2,8-diazabicyclo[ 4.3.0]non-5-en)-8-yl]-1,4-dihydroquinoline-4-oxo- 3-carboxylic acid;

1-cyclopropyl-5-amino-6,8-difluoro-7-[(2,8-diazabicyclo[ 4.3.0]non-5-en)-8-yl]-1,4-dihydroquinoline-4-oxo- 3-carboxylic acid;

1-cyclopropyl-6,8-dichloro-7-[(2-methyl-2,8-diazabicyclo[ 4.3.0]non-5-en)-8-yl]-1,4-dihydroquinoline-4-oxo- 3-carboxylic acid;

1-(2-fluorocyclopropyl)-5,8-dichloro-6-fluoro-7-[(2,8-diazabicyclo[ 4.3.0]non-5-en)-8-yl]-1,4-dihydroquinoline-4-oxo- 3-carboxylic acid;

1-cyclopropyl-6-fluoro-7[(2,8-diazabicyclo[4.3.0]non-5-en)-8-yl]-1,4-dihydroquinoline-4-oxo-3-carboxylic acid;

1-cyclopropyl-6-fluoro-8-methyl-7-[(2,8-diazabicyclo[ 4.3.0]non-5-en)-8-yl]-1,4-dihydroquinoline-4-oxo- 3-carboxylic acid;

1-ethyl-6-fluoro-7-[(2,8-diazabicyclo[4.3.0]non-5-en)-8-yl]1,4-dihydroquinoline-4-oxo-3-carboxylic acid;

1-cyclopropyl-6,8-difluoro-7-[(2-methyl-2,8-diazabicyclo[ 4.3.0]non-5-en)-8-yl]-1,4-dihydroquinoline-4-oxo- 3-carboxylic acid;

1-cyclopropyl-6-fluoro-8-chloro-7-[(2-methyl-2,8-diazabicyclo[ 4.3.0]non-5-en)-8-yl]-1,4-dihydroquinoline-4-oxo- 3-carboxylic acid;

1-cyclopropyl-6-fluoro-8-methoxy-7-[(2-methyl-2,8-diazabicyclo[ 4.3.0]non-5-en)-8-yl]-1,4-dihydroquinoline-4-oxo- carboxylic acid;

1-cyclopropyl-5-amino-6,8-difluoro-7-[(2-methyl-2,8-diazabicyclo[ 4.3.0]non-5-en)-8-yl]-1,4-dihydroquinoline-4-oxo- 3-carboxylic acid;

1-cyclopropyl-6,8-difluoro-7-[(3-methyl-2,8-diazabicyclo[ 4.3.0]non-5-en)-8-yl]-1,4-dihydroquinoline-4-oxo- 3-carboxylic acid;

1-cyclopropyl-6-fluoro-8-chloro-7-[(3-methyl-2,8-diazabicyclo[ 4.3.0]non-5-en)-8-yl]-1,4-dihydroquinoline-4-oxo- 3-carboxylic acid;

1-cyclopropyl-6-fluoro-8-methoxy-7-[(3-methyl-2,8-diazabicyclo[ 4.3.0]non-5-en)-8-yl]-1,4-dihydroquinoline-4-oxo- 3-carboxylic acid;

1-cyclopropyl-5-amino-6,8-difluoro-7-[(3-methyl-2,8-diazabicyclo[ 4.3.0]non-5-en)-8-yl]-1,4-dihydroquinoline-4-oxo- 3-carboxylic acid;

1-cyclopropyl-6,8-difluoro-7-[(5-methyl-2,8-diazabicyclo[ 4.3.0]non-5-en)-8-yl]-dihydroquinoline-4-oxo-3-carboxylic acid;

1-cyclopropyl-6-fluoro-8-chloro-7-[(5-methyl-2,8-diazabicyclo[ 4.3.0]non-5-en)-8-yl]-1,4-dihydroquinoline-4-oxo- 3-carboxylic acid;

1-cyclopropyl-6-fluoro-8-chloro-7-[(2,8-diazabicyclo[ 4.3.0]non-5en)-8-yl]-1,4-dihydroquinoline-4-oxo-3-carboxylic acid lactate;

1-cyclopropyl-6-fluoro-8-methoxy-7-[(5-methyl-2,8-diazabicyclo[ 4.3.0]non-5-en)-8-yl]-1,4-dihydroquinoline-4-oxo- 3-carboxylic acid;

1-cyclopropyl-5-methyl-6-fluoro-7-[(2,8-diazabicyclo[4.3.0]non-5en)-8-yl]-1,4-dihydroquinoline-4-oxo-3-carboxylic acid;

1-cyclopropyl-6,8-difluoro-7-[(3-hydroxymethyl-2,8-diazabicyclo[4.3.0]non-5-en)-8-yl]-1,4-dihydroquinoline-4-oxo- 3-carboxylic acid;

1-cyclopropyl-6,8-difluoro-7-[(3-aminomethyl-2,8-diazabicyclo[4.3.0]non-5-en)-8-yl]-1,4-dihydroquinoline-4-oxo- 3-carboxylic acid;

1-cyclopropyl-5-amino-7-[(5-fluoro-2,8-diazabicyclo[4.3.0]non-5-en)-8-yl]-6,8-difluoro-1,4-dihydroquinoline- 4-oxo-carboxylic acid;

1-cyclopropyl-6,8-difluoro-7-[(2,8-diazabicyclo[4.3.0]non-5-en)8-yl]-1,4-dihydroquinoline-4-oxo- 3-carboxylic acid hydrochloride.

\* \* \* \* \*

UNITED STATES PATENT AND TRADEMARK OFFICE
CERTIFICATE OF CORRECTION

PATENT NO. : 5,498,615
DATED : March 12, 1996
INVENTOR(S) : Kim et al.

It is certified that error appears in the above-indentified patent and that said Letters Patent is hereby corrected as shown below:

Column 7, before line 1, insert --Another compound of formula (III) can be prepared by the following process (II) described in Drugs of the Future, 14, 931 (1989).--;

Column 7, portion of formulas (iii) and (iv) reading "N", should read --≡N--;

Column 8, line 38, under the chemical formula, insert --(XIV)--;

Column 11, line 40, "1-ethyl-6fluoro" should read --1-ethyl-6-fluoro--;

Column 14, line 11, "sampe" should read --same--;

Column 14, line 45, "sampe" should read --same--;

Column 17, line 65, "separated the" should read --separated. The--;

Column 18, line 36, "32.0" should read --32.0 g--;

Column 21, line 55, "and a lower" should read --is a lower--;

UNITED STATES PATENT AND TRADEMARK OFFICE
CERTIFICATE OF CORRECTION

PATENT NO. : 5,498,615
DATED : March 12, 1996
INVENTOR(S) : Kim et al.

It is certified that error appears in the above-indentified patent and that said Letters Patent is hereby corrected as shown below:

Column 22, line 38, "oxo-carboxylic" should read --oxo-3-carboxylic--;

Column 22, line 63, "non-5en" should read --non-5-en--;

Column 23, line 2, "non-5en" should read --non-5-en--;

Column 24, line 3, "4-oxo" should read --4-oxo-3--.

Signed and Sealed this

Twenty-fourth Day of December, 1996

Attest:

BRUCE LEHMAN

*Attesting Officer*       *Commissioner of Patents and Trademarks*